(12) United States Patent
Cousins et al.

(10) Patent No.: US 7,374,903 B2
(45) Date of Patent: May 20, 2008

(54) SUBSTRATES WITH TOPOGRAPHICAL FEATURES FOR THE MANIPULATION OF CELLULAR BEHAVIOR AND RESPONSE

(75) Inventors: Brian G. Cousins, Liverpool (GB); Michael Joseph Garvey, Wirral (GB); John Fink, Liverpool (GB); Rachel Lucinda Williams, Neston (GB); Patrick Joseph Doherty, Crosby (GB)

(73) Assignee: The University of Liverpool (GB)

( * ) Notice: Subject to any disclaimer, the term of this patent is extended or adjusted under 35 U.S.C. 154(b) by 125 days.

(21) Appl. No.: 10/480,780

(22) PCT Filed: Jun. 11, 2002

(86) PCT No.: PCT/GB02/02652

§ 371 (c)(1),
(2), (4) Date: Jun. 9, 2004

(87) PCT Pub. No.: WO02/101028

PCT Pub. Date: Dec. 19, 2002

(65) Prior Publication Data

US 2004/0219670 A1   Nov. 4, 2004

(30) Foreign Application Priority Data

Jun. 13, 2001   (GB) .................. 0114399.9

(51) Int. Cl.
*C12Q 1/02* (2006.01)
(52) U.S. Cl. .................................................. 435/29
(58) Field of Classification Search ............ 435/29, 435/287.8, 287.9
See application file for complete search history.

(56) References Cited

U.S. PATENT DOCUMENTS

2005/0227373 A1* 10/2005 Flandre et al. .............. 436/518

FOREIGN PATENT DOCUMENTS

| CA | 2302118 | 9/2000 |
|----|---------|--------|
| CA | 2323719 | 4/2001 |
| DE | 198 18 956 | 11/1998 |
| EP | 1 040 874 A2 | 10/2000 |
| EP | 1 095 760 A1 | 5/2001 |
| WO | WO 97/12966 | 4/1997 |
| WO | WO 97/12966 A1 * | 4/1997 |
| WO | WO 00/66036 | 11/2000 |

OTHER PUBLICATIONS

Flemming R. G. et al. Effects of Synthetic Micro and Nano Structured Surfaces on Cell Behavior. Biomaterials vol. 20, paes 573-588, 1999.*
E.T. den Braber et al. (1996) "Quantitative analysis of cell proliferation and orientation on substrata with uniform parallel surface micro-grooves" *Biomaterials* vol. 17 No. 11 pp. 1093-1099, Elsevier Science Limited.
Goodman et al. (1996) "Three-dimensional extracellular matrix textured biomaterials" *Biomaterials* vol. 17, No. 21, pp. 2087-2095 (Elsevier Science Limited).
Wojciak-Stothard et al. (1996) "Guidance and Activation of Murine Macrophages by Nanometric Scale Topography" *Experimental Cell Research* vol. 223, pp. 426-435, Article No. 0098, Academic Press, Inc.
Oakley et al. (1997) "Sensitivity of Fibroblasts and Their Cytoskeletons to Substratum Topographies: Topographic Guidance and Topographic Compensation by Micromachined Grooves of Different Dimensions" *Experimental Cell Research* vol. 234 pp. 413-424 Article No. EX973625, Academic Press, Inc.
Flemming et al. (1999) "Effects of synthetic micro- and nano-structured surfaces on cell behavior" *Biomaterials* vol. 20 pp. 573-588, Elsevier Science Ltd.

* cited by examiner

*Primary Examiner*—Ralph Gitomer
(74) *Attorney, Agent, or Firm*—Waddey & Patterson, P.C.; Emily A. Shouse; Ryan D. Levy

(57) ABSTRACT

The present invention relates to novel substrates, to methods of making them and to uses therefor. The substrates of the invention comprise a base portion and a surface layer covering at least part of the base portion, with a binding layer provided therebetween. The surface layer provides, on at least a part of the substrate, topographical features having at least one nano scale dimension. These topographical features are adapted to facilitate, influence, control or inhibit cell or tissue growth thereon and/or therebetween and the substrate may be used for the study, manipulation or modification of at least one cellular or tissue behavior or response.

12 Claims, 8 Drawing Sheets

SUBSTRATES WITH TOPOGRAPHICAL FEATURES FOR THE MANIPULATION OF CELLULAR BEHAVIOR AND RESPONSE

This application is a National Stage application filed under 371 based on PCT/GB02/02652 filed Jun. 11, 2002, which claims priority to UK 0114399.9 filed Jun. 13, 2001.

The present invention relates to novel substrates, to methods of making them and to uses therefor. In particular the invention concerns such materials, methods and uses for the study, manipulation or modification of cell or tissue behaviour.

The behaviour of cells are influenced by their external environment, both chemical and physical. Understanding interactions which take place between a cell and its substrate is important in connection with such fields as medical implants and prostheses, tissue engineering and pharmaceutical development. One substrate characteristic which has been shown to influence cellular behaviour is topography and synthetic structured surfaces have been used to investigate this influence. A review of such investigations may be found in *Biomaterials* (1999), 20, 573-588. In vivo studies are reported in *Biomaterials* (1996), 17, 2087-2095.

The modification of surface topography for the control of cellular response is an important area of research in medical engineering that targets several potential end uses, particularly relating to the biocompatibility of materials used in medical and dental devices and implants and in the preparation of materials, such as hygienic surfaces, which deter cell growth thereon. In this area, it is required to control the interfacial reactions that mitigate the appropriate response for a specific application. It is known that the interfacial reactions are influenced by the surface properties of the substrate in terms of the surface chemistry, energy and topography. Of the latter, current research is focused on etching techniques to create the desired topography. *Experimental Cell Research* (1996), 223, 426-435, discusses the production of micro fabricated grooves and steps by means of dry etching a silica substrata with a reactive ion etching unit. U.S. Pat No. 4,832,759 also discusses the generation of a plurality of surface discontinuities by means of ion beam etching. Many prior art studies have used photolithographic techniques to engineer surface features with controlled morphology for the study of cell behaviour thereon. Other techniques include glancing angle deposition, laser ablation, laser deposition, replica molding of x-ray lithography masters, imprint lithography, micro contact printing and etching and ink-jet printing. For example, Canadian Pat No. 2,323,719 discusses the production of structural elevations by the LIGA lithographic process which incorporates x-ray lithography, electrodeposition and molding. Canadian Pat No. 2,302,118 discloses microstructured surfaces produced mechanically or lithographically. DE-A-19818956 discloses materials with a micro-roughened, bacteria-repellant surface. WO-A-97/12966 discloses methods for producing thin colloidal silica films on substrates by spin coating or spraying the substrate with colloidal silica, or dipping the substrate in a colloidal silica solution.

Cell-substrate interactions in the natural environment are influenced by the surface topography of the substrate, the topographical features of which are represented at the nanoscale level. Some of the above-mentioned techniques and prior art disclosures for engineering synthetic surface features are capable of generating topographical features at the nanoscale level but none has so far offered a quick and convenient means to study, manipulate or modify cellular behaviour at this level and the suitability for commercial application of many of these known substrates is limited. One particular problem with some prior art substrates is the tendency of the micro-structured surface layer to crack or peel.

It is an object of the present invention to provide a substrate which can be used to study, manipulate or modify cellular behaviour at the nanoscale level. It is a further object of the invention to provide such a substrate which is sufficiently robust to be useful in commercial applications. Another object of the invention is to provide a substrate which can be manufactured reproducibly, conveniently and without excessive expense.

According to the present invention there is provided a substrate for the study, manipulation or modification of at least one cell or tissue behaviour or response, the substrate comprising:

a base portion;

a surface layer covering at least part of the base portion, the surface layer providing the substrate with topographical features having at least one nanoscale dimension of from about 1 to about 200 nm, said topographical features having the capacity to adapt, facilitate, influence, control or inhibit at least one cell or tissue behaviour or response thereon and/or therebetween; and a binding layer between the base portion and the surface layer, the binding layer comprising a material capable of binding to the base portion and a material capable of binding to the surface layer to maintain the surface layer in place.

The substrate of the invention provides a novel material which may find application in a wide variety of circumstances. For example, substrates according to the invention may be used to provide medical implants which discourage cell growth thereon. Hygienic surfaces, for use in hospitals, restaurants, kitchens, etc. may be formed from substrates according to the invention. Prior art substrates having nanoscale topography have tended to be unsuitable for many commercial applications as they are not sufficiently robust to withstand exposure to the conditions of such applications. Many prior art substrates have nanoscale topography which cracks, flakes or peels over time, rendering the substrate unsuitable for most applications other than short term academic study.

In the context of this document, "nanoscale" is used to refer to topographical features having at least one dimension which is measurable at the nanometre level, for example a feature which measures from about 1 to about 200 nm, preferably from about 1 to about 150 nm, even more preferably from about 1 to about 100 nm, and most preferably less than about 50 nm in at least one dimension.

The topographical features may form a random array on the surface layer of the substrate. Such an array may comprise, for example, an agglomeration of peaks and troughs, preferably having substantially the same or similar dimensions and physical characteristics.

Alternatively, the topographical features may form an ordered array on the surface layer of the substrate. A combination of random and ordered arrays may be used also. Whatever form of array adopted by the topographical features, the substrate of the invention preferably comprises nanoscale topographical features separated from other nearest neighbour similar nanoscale topographical features by distances of up to about 1000 nm. For example, when the array comprises individual peaks and troughs, each peak in the array may be separated from its nearest neighbour peaks by distances of up to about 500 nm, preferably no more than about 200 nm. Where the array comprises a series of longitudinal ridges, each ridge in the array may be separated from its nearest neighbour by distances of up to about 1000 nm, preferably no more than about 500 nm.

Preferably the base portion and the surface layer are of different materials and preferably the material of the binding layer is different from one or both of the materials of the base portion and the surface layer. The binding layer may comprise a single layer comprising one or more materials, provided that the binding layer comprises at least one material capable of binding to the base portion and at least one material capable of binding to the surface layer. The same material of the binding layer may bind to both the base portion and to the surface layer, in which case the binding layer may comprise a single material. However, the binding layer may comprise a plurality of materials and may be a composite layer. Thus, for example the binding layer may comprise two layers containing, respectively, a first material and a second material. The first material may be capable of binding to the base portion and to the second material. The second material may be capable of binding to the first material and to the surface layer. The substrate of the invention may comprise additional layers between the surface layer and the base portion. Such additional layers may comprise one or more bilayers of surface layer material and binding layer material.

Further provided in accordance with the invention is a use of a substrate according to the invention for the study, manipulation or modification of at least one cell or tissue behaviour or response.

The topographical features are preferably provided by means of controlled deposition onto the base portion of a surface layer capable of adhering to the substrate. Such adherence may be chemical or physical.

Thus, in one of its aspects this invention relates to methods for tailoring the surface topography of substrates using the controlled deposition of thin films of nanoscale material onto an underlying base portion so as to modify cell or tissue response to the treated surface.

The present invention further provides a method for manufacturing a substrate useful for the study, manipulation or modification of at least one cell or tissue behaviour or response comprising the steps of:

a) providing a base portion, a material suitable for forming a surface layer on the base portion, and a binding material suitable for forming a binding layer between the base portion and the surface layer;

b) contacting the base portion with the binding material under conditions effective for at least partial binding of the binding material to the base portion;

c) contacting the at least partially bound binding material with the surface layer material under conditions effective for at least partially binding the surface layer to the binding material to form a surface layer at least partially covering the base portion, the surface layer comprising topographical features having at least one nanoscale dimension of from about 1 to about 200 nm, said topographical features having the capacity to adapt, facilitate, influence, control or inhibit at least one cell or tissue behaviour or response thereon and/or therebetween; and d) if necessary completing binding of the binding material to the base portion and/or the surface layer.

Also provided in accordance with the invention is a method for manufacturing a substrate useful for the study, manipulation or modification of at least one cell or tissue behavior or response comprising the steps of:

a) providing a base portion, a material suitable for forming a surface layer on the base portion, and a binding material suitable for forming a binding layer between the base portion and the surface layer;

b) contacting the surface layer material with the binding material under conditions effective for at least partial binding of the binding material to the surface layer material;

c) contacting the at least partially bound binding material with the base portion under conditions effective for at least partially binding the base portion to the binding material to form a surface layer at least partially covering the base portion, the surface layer comprising topographical features having at least one nanoscale dimension of from about 1 to about 200 nm, said topographical features having the capacity to adapt, facilitate, influence, control or inhibit at least one cell or tissue behaviour or response thereon and/or therebetween; and d) if necessary completing binding of the binding material to the base portion and/or the surface layer.

Thus, in one of its aspects the invention provides a substrate, modified with a surface of deposited nanoscale material in order to control the cellular response that occurs as a result of cell contact or interaction. Further provided is a process of tailoring surface topography by the deposition of nanoscale material onto an underlying substrate material so as to change the cellular response that occurs as a result of cell contact or interaction with that surface.

In one preferred embodiment of the invention there is provided a substrate for the study, manipulation or modification of at least one cellular or tissue behavior or response, the substrate comprising a base portion being provided on a surface thereof, by means of controlled deposition onto the base portion, of a substance capable of adhering to the base portion, with topographical features having at least one nanoscale dimension and a cell or tissue growth, growth inhibition or growth control region thereon and/or therebetween, the topographical features being deposited in a densely packed array with a separation between nearest neighbour similar topographical features of not more than 1000 nm.

In another preferred embodiment of the invention there is provided a method of manufacturing a substrate for the study, manipulation or modification of at least one cellular or tissue behavior or response comprising providing a base portion, depositing onto the base portion a substance capable of adhering thereto in order to provide the substrate with topographical features having at least one nanoscale dimension the deposit being densely packed with separation between the topographical features of not more than 1000 nm, and providing the substrate with a cell or tissue growth, growth inhibition or growth control region on and/or between the topographical features.

The base portion may be selected from any suitable material, depending for example on whether it is intended to promote, inhibit or control cell or tissue growth on the base portion material itself or only on the covering surface layer. The end use of the substrate may also help determine the choice of base portion material, a relatively rigid material being used in the manufacture hygienic work surfaces, for example. The base portion may comprise a single material or may comprise two or more layers of different materials. The base portion is preferably formed from a material selected from polymers, glasses, ceramics, carbon, metals, composites and paper (including tissue paper). The base portion may also comprise an existing surface that is modified in accordance with the present invention. This may for example be an existing work surface or swimming pool surface, to which a surface layer is applied.

The surface layer is preferably formed from a material selected from polymers, glasses, ceramics, carbon, metals and composites. Suitable surface layer materials include silica, gold and silver. The surface layer may comprise colloidal particles of these or other materials and such colloidal particles may be nano-particulate, for example having mean diameters of from about 5 to about 80 nm.

The binding layer may comprise one or more substances capable of adhering to the base portion and the surface layer material. Suitable binding layer materials include polymers, surface active agents, reactive chemical ligands and polycationic materials. Preferably the adhering substance is insoluble or sparingly soluble. Inorganic, organic, metallic and polymeric materials, or mixtures of one or more thereof, may be used.

The substrates, methods and uses of the invention have advantages over conventional engineered surfaces used in medical engineering and methods for making them. Cell behavior can be manipulated and controlled by selecting different topographies as cells respond differently to different physical environments. The invention therefore provides a valuable tool for use in medical engineering. The substrates of the invention may also be adapted to provide robust surfaces for use, for example, in hospitals, restaurants and kitchens where it is desirable to discourage eukaryotic and prokaryotic cell growth on surfaces such as bench tops, walls and floors.

The invention will now be more particularly described with reference to the following Figures and Examples in which.

EXAMPLE 1

Figure 1:
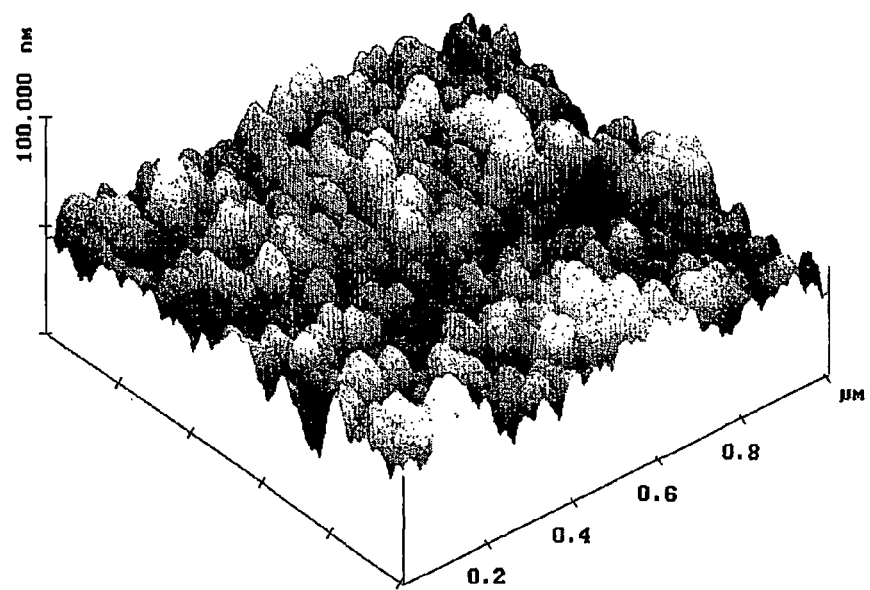
FIG. 1 shows an image of a first substrate in accordance with the invention, the image being generated by means of atomic force microscopy (AFM).

Three 10×10×1 mm$^2$ optically clear polystyrene (PS) squares were cut out from a plasma treated polystyrene culture dish. Each PS segment was then washed once with methanol followed by copious rinsing with deionised water (Millipore-Q 18.2 M). Each cleaned PS sample was then half immersed in an aqueous solution of 1 g L$^{-1}$ polycationic polymer (Zetag)™ for approximately 15 minutes to allow for the development of a monolayer of polycationic polymer on the PS surface. The polycationic derived PS samples were then removed from the polymer solution and washed copiously with deionised water (Millipore-Q 18.2 M ) to remove excess polycationic polymer. The coated portions of each PS sample were then immersed in three different aqueous dispersions of silica solution (Ludox TM-50; HS-40 and SM-30, ex. Dupont de Nemours & Co.) containing approximately 40% w/w silica particles of approximately 21, 14 and 7 nm diameter respectively. A further aqueous dispersion of silica solution was also used which contained approximately 10% w/w silica particles of approximately 80 nm in diameter. The surfaces of each silica coated PS sample were then scanned using atomic force microscopy (AFM). An AFM image of the surface of a 21 nm coated sample is shown in FIG. 1., which shows a random close packed array of silica particles.

The samples of silica coated PS were then used as substrates in cell culture experiments. A suspension of clone L 929 mouse fibroblast established cell line was prepared from a culture maintained in Eagle's Minimum Essential medium with a 5% foetal calf serum supplement. The suspension was prepared at cell concentration of approximately 1×10$^5$ cell/mi. This was performed by immersing each PS sample in a cell culture medium containing established fibroblast cells for approximately 24 hours in an incubator at 37° C.

Figure 3:
FIG. 3 shows an image generated by a light microscope of cells on a substrate in accordance with the invention.
Figure 5:
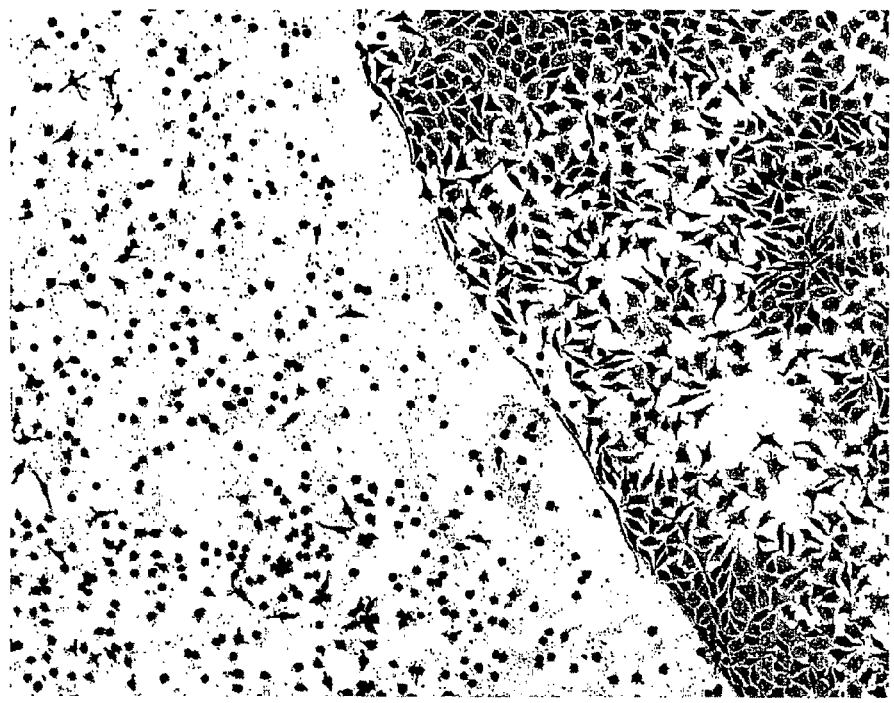
FIG. 5 shows an image generated by a light microscope of a further example of cells on a substrate in accordance with the invention as shown in FIG. 3.

After this period the PS samples were removed from the culture medium and examined with an inverted phase-contrast light microscope. An image observed on 14 nm silica coated PS is shown in FIGS. 3 and 5. It can be seen that the cells develop as flat, extended entities on the surface of the clean PS indicating a strong affinity for the cells to attach and develop on the surface with a confluent morphology. This is in contrast to the treated segment of the PS culture dish where the cells remain spherical in solution and do not adhere to the silica coated PS surface.

Figure 2:
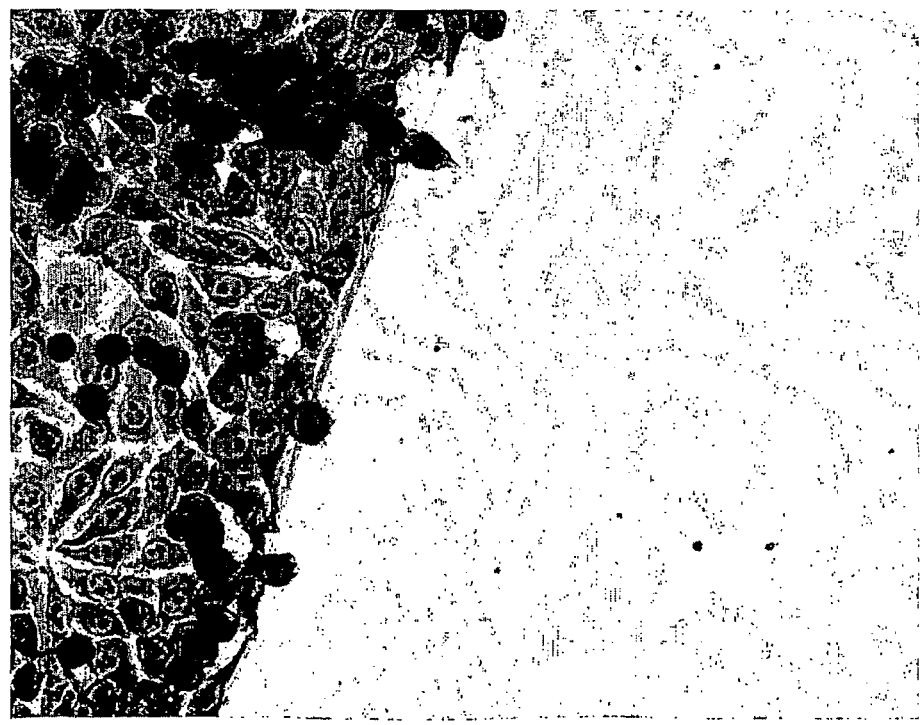
FIG. 2 shows an image generated by a light microscope of cells on a substrate in accordance with the invention.
Figure 4:
FIG. 4 shows an image generated by a light microscope of a further example of cells on a substrate in accordance with the invention as shown in FIG. 2.

In a variant of the previous experiment, the cell suspension was only applied to the untreated substrate and the cells were allowed to spread to the interface during a 48 hour incubation period. FIGS. 2 and 4, shows the results of this experiment and clearly shows the interface between the treated and untreated base substrates. The cells did not cross the interface. Adhesion is again inhibited on the nano-particulate coated substrate and cells on the untreated substrate have assumed a normal morphology.

Figure 6:
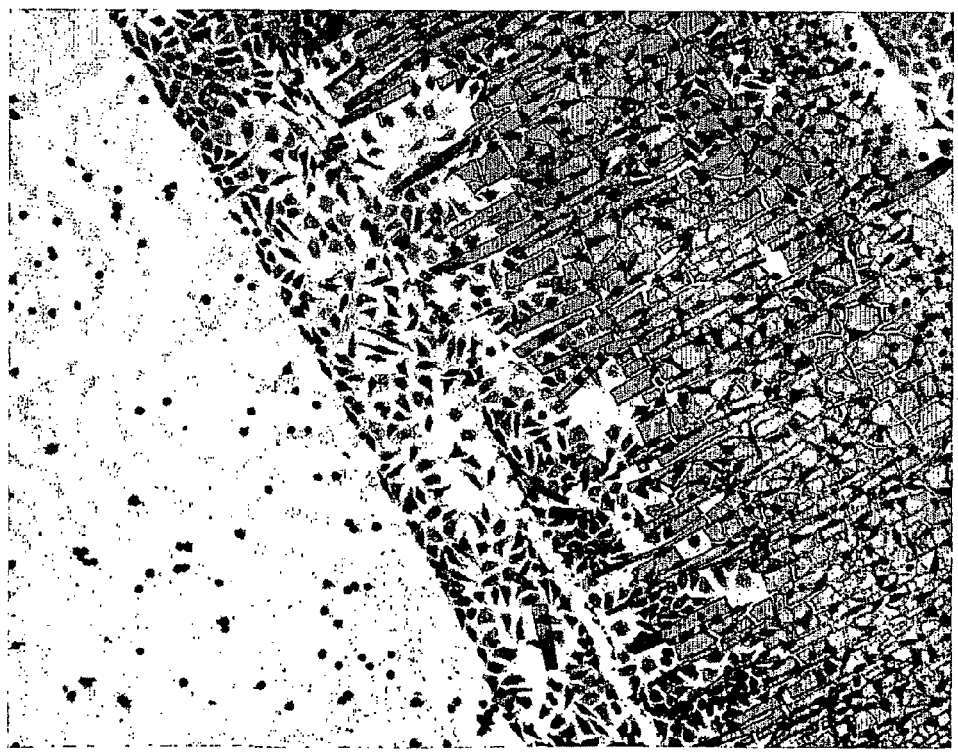
FIG. 6 shows an image generated by a light microscope of cells on the edge of a poorly adhered surface layer on a substrate in accordance with the invention.
Figure 7:
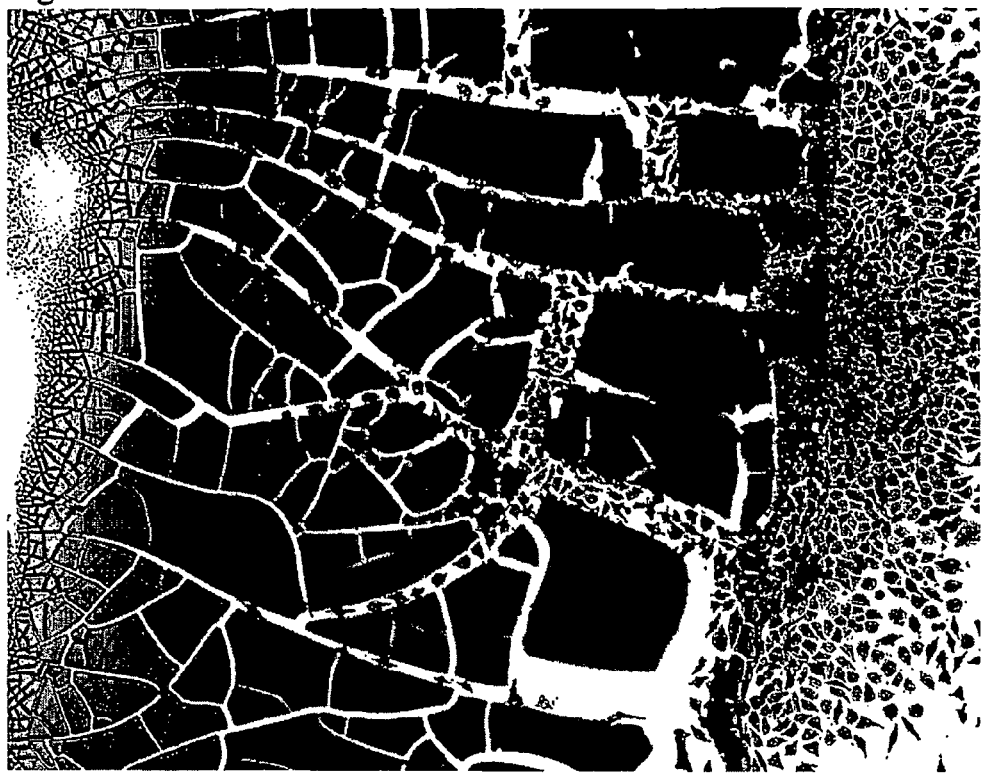
FIG. 7 shows an image generated by a light microscope of cells on the edge of a poorly adhered surface layer on a substrate in accordance with the invention.
Figure 8:
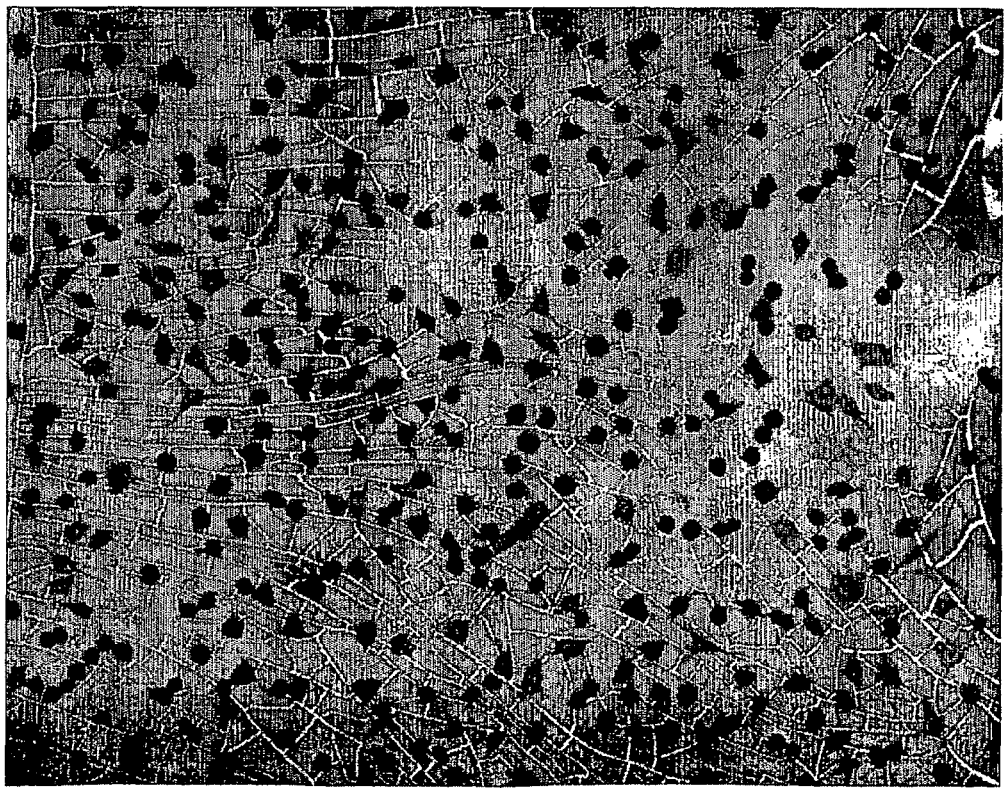
FIG. 8 shows a high magnification image generated by a light microscope of cells on the edge of a poorly adhered surface layer on a substrate in accordance with the invention.

FIG. 6, shows the fibroblast cells at silica boundary. The silica boundary is clearly identified with silica coated surface. Cells on silica surface showed a rounded morphology. At the boundary there is a clearly identifiable dried/cracked silica layer, which was produced by a poorly adhered first layer of particles. Cells were showing a spread morphology on this surface, but appeared to grow well in the voids in the silica and on the untreated surface. FIG. 8 is a higher magnification image of FIG. 6, and further illustrates the preference that the cells had for growth in the cracks within the silica FIG. 7, is an image of a different part of the cracked silica and illustrates again the spread of fibroblast cells invading the cracks in the silica.

In a variant of the previous experiment, the cell suspension was only applied to the untreated substrate and the cells were allowed to spread to the interface during the 48 hour incubation period. As can be seen in FIG. 4, the cells did not cross the interface. Adhesion is again inhibited on the nano-particulate coated substrate and cells on the untreated substrate have assumed a normal morphology. Cells on the treated substrate retain a rounded morphology and are inhibited from spreading.

EXAMPLE 2

In order to assess the growth characteristics of different cells on the substrate, bovine lens epithelial cells were applied to the glass substrate partially coated with nano-particulate material.

Primary bovine lens epithelial cells were obtained from the Unit of Opthalmology, The University of Liverpool at second or third passage and maintained in Dulbecco's Minimal essential Medium supplemented with 10% foetal calf serum. A cell suspension was prepared at a cell concentration of approximately $5 \times 10^4$ cells/ml. 1 ml of this cell suspension was directly applied to both treated and untreated surface of a substrate prepared as described in Example 1. The cells were left in contact with the substrate for 30 minutes to allow cells adhesion, then the substrate was flooded with culture medium and maintained at 37° C./5% $CO_2$ for 48 hours. After this time the culture medium and non-adherent cells were removed. The substrate was then treated with 100% methanol in order to fix the cells and the substrate was stained with 0.04% methylene blue for 10 minutes.

Figure 9:
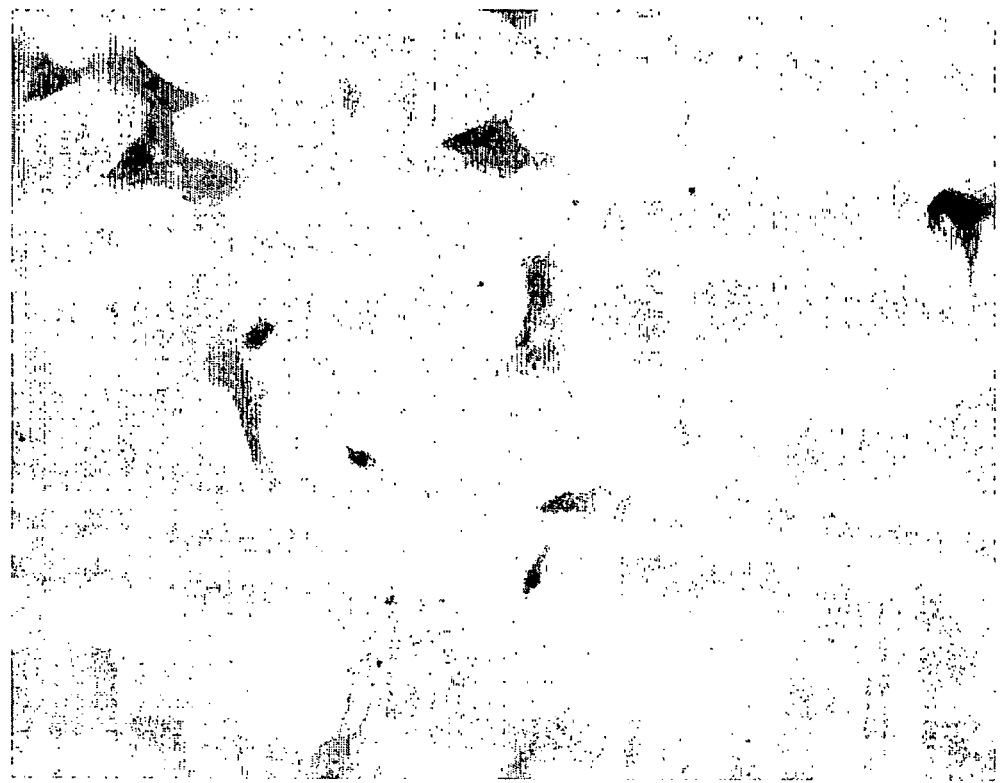
FIG. 9 shows an image generated by a light microscope of cells on a substrate in accordance with the invention.
Figure 10:
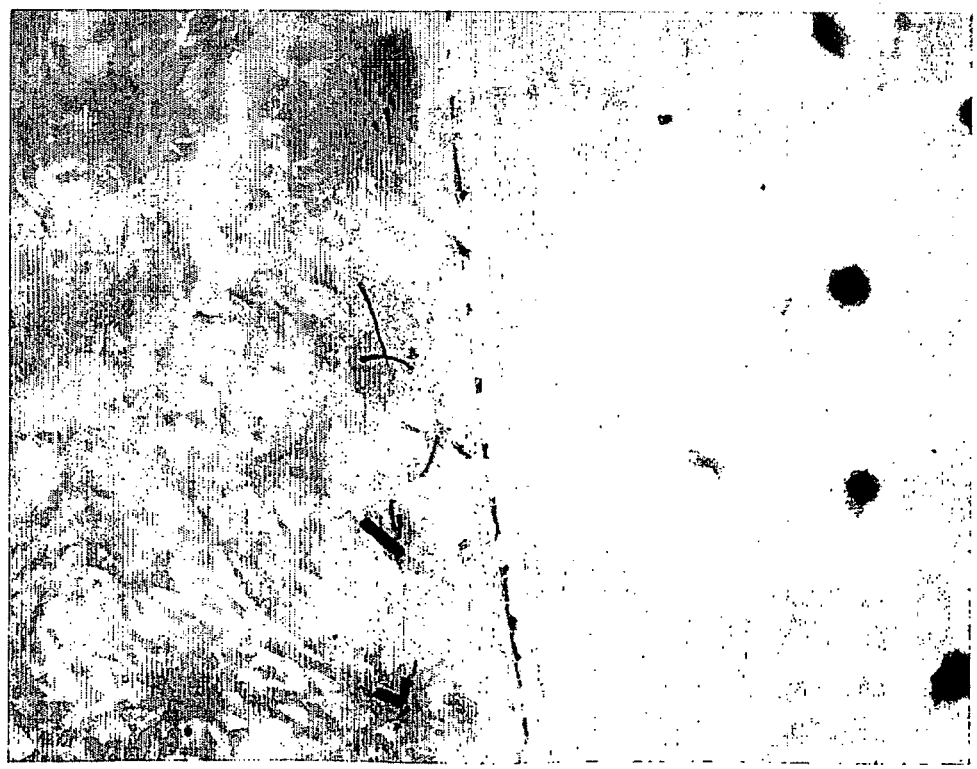
FIG. 10 shows an image generated by a light microscope of cells on a substrate in accordance with the invention.

FIG. 9 shows an optical micrograph highlighting the interface between the treated and untreated base substrate. Cells on the treated substrate are fewer in number and have a changed morphology. There appears to be some inhibition of cell spreading. Furthermore, FIG. 10 which shows the results of an experiment that used primary bovine fibroblasts as opposed to epithelial cells as outlined above also highlights the interface between the treated and the untreated base substrate. Cells on the untreated substrate have assumed a normal morphology, whilst cells on the treated substrate retained a rounded morphology and have remained in clumps and are inhibited from spreading.

In conclusion, epithelial cells were shown to behave in a similar manner to L 929 fibroblast cells on the treated and untreated substrate and it could also be postulated that other cell types would behave in a similar manner.

EXAMPLE 3

PMMA and similar materials are often modified with an air glow discharge plasma in order to improve their wettability. Therefore an experiment was conducted in order to assess the growth of fibroblast cells on a PMMA substrate which had been treated with an air plasma.

Figure 11:
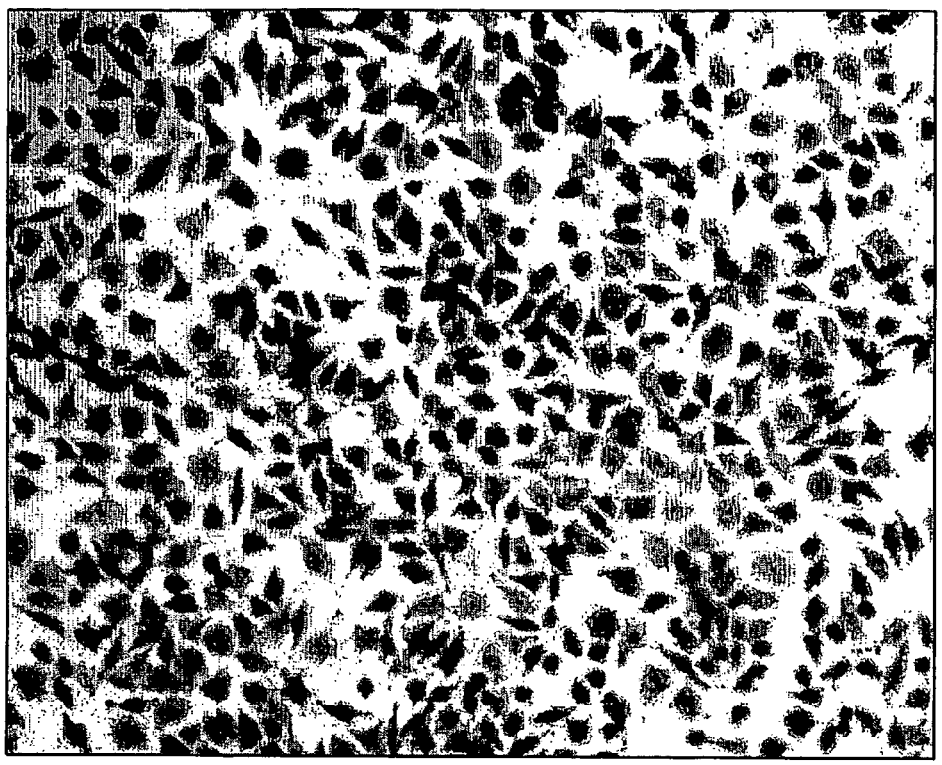
FIG. 11 shows an image generated by a light microscope of cells on a control substrate following air plasma treatment.

A suspension of clone L 929 mouse fibroblast established cell line was prepared from a culture maintained in Eagle's Minimum Essential medium with a 5% foetal calf serum supplement. The suspension was prepared at cell concentration of approximately $1 \times 10^5$ cell/ml. 1 ml of the cell suspension was directly applied to the surface of an air plasma treated polymethylmethacrylate substrate which was prepared according to a standard protocol. The cells were left in contact with the substrate for 30 minutes to allow cells adhesion, then the substrate was flooded with culture medium and maintained at 37° C./5% $CO_2$ for 48 hours. After this time the culture medium and non-adherent cells were removed. The substrate was then treated with 100% methanol to fix the cells and the substrate was stained with 0.04% methylene blue for 10 minutes. FIG. 11 shows the results of this experiment and is an optical micrograph detailing normal confluent cell coverage and morphology on the substrate.

The L929 fibroblast cells were then tested on a PMMA substrate following air plasma treatment and subsequent nano-particulate coating.

Figure 12:
FIG. 12 shows an image generated by a light microscope of cells on a substrate following air plasma treatment in accordance with the invention.

The method was the same as outlined above and the cells were directly applied to the surface of an air plasma polymethylmethacrylate substrate as described in Example 1 with a subsequent nano-particulate coating. FIG. 12 shows the results of the experiment and is an optical micrograph demonstrating that the cell adhesion has been significantly inhibited when compared to the normal growth seen on FIG. 11.

EXAMPLE 4

The cell growth modifying effects of a layer of silica nano-particles on PMMA, polystyrene and glass had been assessed in Examples 1 to 3. Further studies were directed to alternative nano-particles which could be used, one such material was gold.

Figure 13:
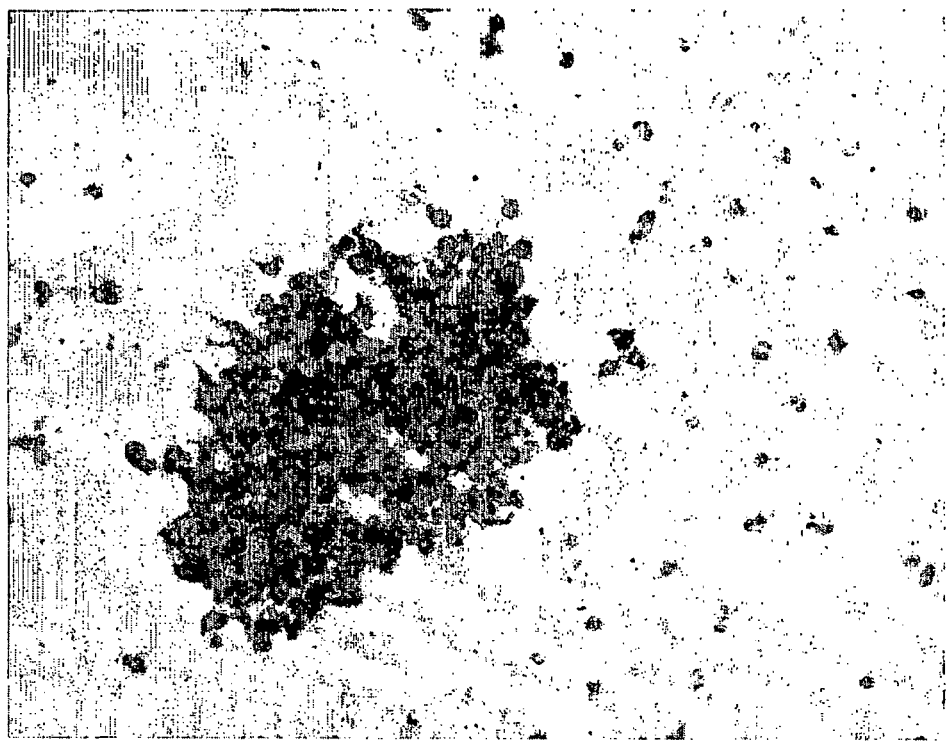
FIG. 13 shows an image generated by a light microscope of cells on a substrate incorporating gold particles in accordance with the invention.

A gold particulate preparation of a 30 mM aqueous solution of hydrogen tetrachloroaurate (Aldrich) was mixed with 80 ml of a 50 mM solution of tetraoctyl ammonium bromide (Fluka) in toluene (AnalaR grade) forming a two phase mixture. The organic layer containing the $[AuC_{14}]^-$ and $[N(C_8H_{17})_4]^+$ ions was then washed three times with de-ionised water. 25 ml of freshly prepared 0.4 M aqueous sodium borohydride (Fisons) was then added in small aliquots with vigorous stirring. The resulting colloidal gold solutions (approx. 5 nm in diameter) were deployed using the same procedure describe for the use of silica particles in Example 1. FIG. 13 shows the results of the experiment in an optical micrograph detailing following L929 contact with this substrate. The fibroblast cells display an abnormal morphology and there is evidence of cell lysis on the Au organosol nano-particulate substrate.

EXAMPLE 5

Additional experiments were directed to non-mammalian cells. *Staphylococcus aureus* was chosen to investigate whether the nano-particle substrate could alter growth characteristics of prokaryotic cells.

Figure 14:
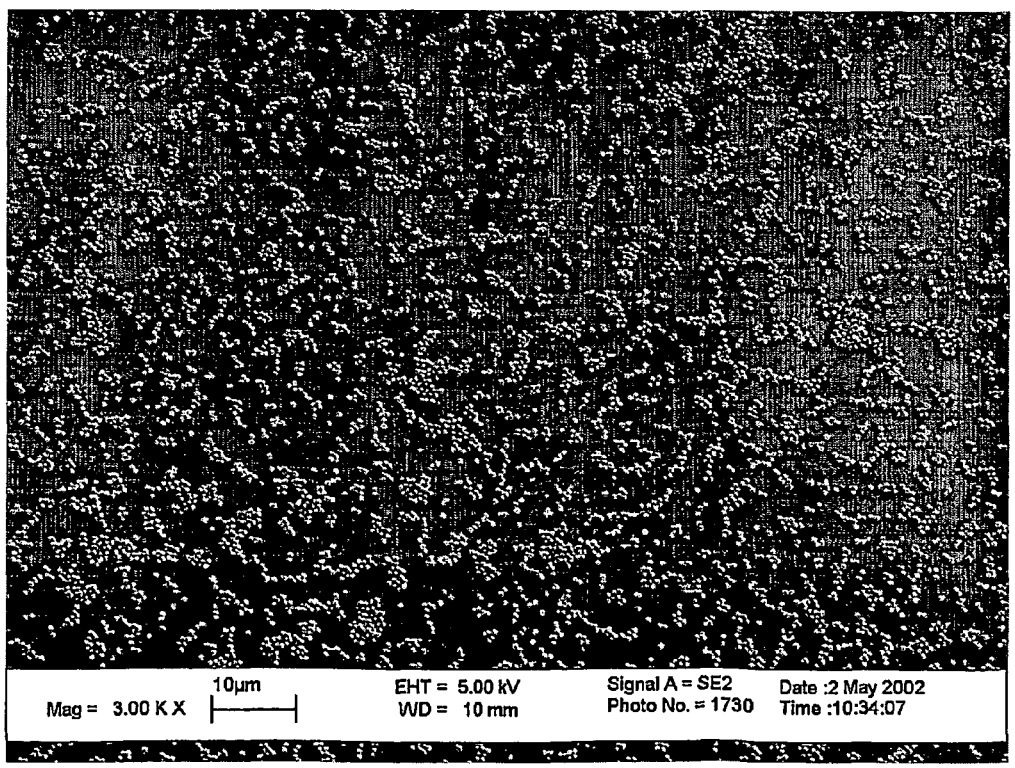
FIG. 14 shows an image generated by a light microscope of S. aureus cells on a control glass substrate

A strain of *S. aureus* bacteria was prepared in fill growth broth then placed directly in contact with a plain glass base substrate. A 1 ml suspension of the bacteria was presented to the substrate at a concentration of approximately $10^7$ cells/ml The bacterial remained in contact with the substrate for 60 minutes. The substrate was then washed with distilled water and prepared for scanning electron microscopy by fixing in 2.5% gluteraldehyde and dehydrating in a series of alcohols. FIG. 14 shows a scanning electron micrograph [×3000] which details the population of bacteria remaining on the substrate and it provides a quantification of *S. aureus* cells after 60 minutes of incubation on plain glass.

Figure 15:
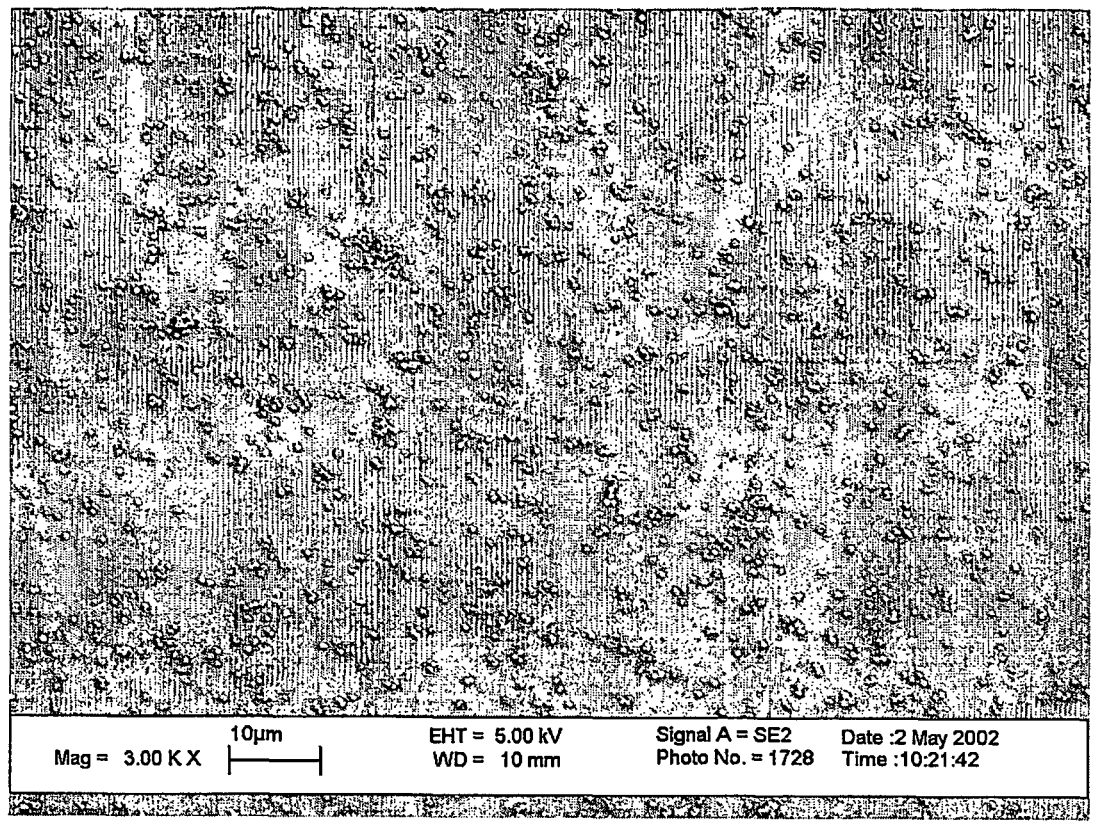
FIG. 15 shows an image generated by a light microscope of S. aureus cells on a substrate incorporating gold particles in accordance with the invention.

A further experiment was conducted that utilised the same strain of *S. aureus* cells and provided to a slide by the same procedure as outlined above. The *S. aureus* was presented to plain glass substrate coated with Au organosol which was prepared in accordance to the protocol outlined in Example 4. FIG. 15 shows a scanning electron micrograph [×3000] which details the population of bacteria remaining on the substrate after 60 minutes of incubation. There is a quantifiably lesser number of bacteria associated with the nanoparticulate substrate, which suggests that the nanoparticulate substrate inhibits the growth of *S. aureus*.

The invention claimed is:

1. A method of limiting cellular proliferation of cells on a surface, comprising the steps of:
    a) providing a base portion with a surface;
    b) applying a binding layer to the surface of the base portion to create a binding surface; and
    c) applying a colloid having particles of from about 5 nanometers to about 80 nanometers to the binding surface to form an arrayed surface to limit cellular proliferation wherein the binding surface comprises a substantially different material than the arrayed surface.

2. The method of claim 1 wherein the arrayed surface limits the cellular proliferation in step c) by altering the cellular morphology of the cells.

3. The method of claim 1 wherein the binding surface of step b) comprises a cationic binding surface.

4. The method of claim 3 wherein the particles of step c) comprise silica.

5. The method of claim 4 wherein step c) further comprises ionically bonding the silica to the cationic binding surface.

6. The method of claim 4 wherein step d) further comprises limiting cellular proliferation of eukaryotic cells.

7. The method of claim 4 wherein step d) further comprises limiting cellular proliferation of prokaryotic cells.

8. A method of limiting cellular proliferation of cells on a surface, comprising the steps of:
    a) providing a base portion with a surface;
    b) combining a binding layer with particles having an average diameter of from about 5 nanometers to about 80 nanometers to form a surface layer mixture; and
    c) applying the surface layer mixture to the surface of the base portion to form an arrayed surface to limit cellular proliferation.

9. The method of claim 8 wherein the arrayed surface limits the cellular proliferation in step c) by altering the cellular morphology of the cells.

10. The method of claim 8 wherein step d) further comprises limiting cellular proliferation of eukaryotic cells.

11. The method of claim 8 wherein step d) further comprises limiting cellular proliferation of prokaryotic cells.

12. A method of limiting cellular proliferation of cells on a surface, comprising the steps of:
    a) providing a base portion with a surface;
    b) providing a binding material;
    c) providing a surface layer material with solid particles of from about 1 nanometer to about 80 nanometers with the surface layer material comprising a different material than the binding material of step b);
    d) simultaneously applying the binding material and the surface layer material to at least partially bind to the surface of the base portion to form an arrayed surface on the base portion to limit cellular proliferation.

* * * * *